United States Patent [19]
Karlen et al.

[11] Patent Number: 6,004,545
[45] Date of Patent: Dec. 21, 1999

[54] HAIR CLEANSING COMPOSITION WITH FIXING PROPERTIES

[75] Inventors: Thomas Karlen, Bern, Switzerland; Jürgen Schmenger, Weiterstadt; Karin Steinbrecht, Ober-Ramstadt, both of Germany

[73] Assignee: Wella AG, Darmstadt, Germany

[21] Appl. No.: 08/939,739

[22] Filed: Oct. 6, 1997

[30] Foreign Application Priority Data

Oct. 16, 1996 [DE] Germany .............................. 196 42 623

[51] Int. Cl.$^6$ ....................................................... A61K 7/11
[52] U.S. Cl. ..................... 424/70.12; 424/70.19; 424/70.21; 424/70.22; 424/70.31; 424/47
[58] Field of Search .............................. 424/70.12, 70.19, 424/70.21, 70.22, 70.31, 47

[56] References Cited

FOREIGN PATENT DOCUMENTS

| | | |
|---|---|---|
| 0412704A2 | 2/1991 | European Pat. Off. . |
| 0412707A1 | 2/1991 | European Pat. Off. . |
| WO 93/23446 | 11/1993 | WIPO . |
| WO93/23009 | 11/1993 | WIPO . |
| WO 95/04518 | 2/1995 | WIPO . |
| WO95/03776 | 2/1995 | WIPO . |
| WO 95/32703 | 12/1995 | WIPO . |

*Primary Examiner*—Jyothsna Venkat
*Attorney, Agent, or Firm*—Michael J. Striker

[57] ABSTRACT

The hair cleansing composition contains from 0.1 to 30 percent by weight of a dimethylsiloxanelmethyl-3-mercapto-propylsiloxane/isobutylmethacrylate copolymer and from 3 to 50 percent by weight of at least one detergent surfactant. The composition can also contain dimethylsiloxane glycol copolymers and/or polydimethylsiloxanes with or without hydroxy terminal groups. This composition has a definite fixing effect as well as satisfactory hair cleaning action. The film formed on the hair after washing and drying the hair does not significantly load the hair or leave an appreciable residue.

6 Claims, No Drawings

HAIR CLEANSING COMPOSITION WITH FIXING PROPERTIES

BACKGROUND OF THE INVENTION

The subject matter of the present invention is a hair cleansing composition containing at least one nonionic, water-insoluble vinyl/silicone copolymer with a backbone chain of siloxane polymer units and side chains of vinyl polymer units and at least one detergent surfactant.

Hair cleansing or cleaning compositions usually contain hair care additives besides the surfactant having the cleansing or detergent action, which should guarantee that the hair can be combed in both the wet and the dry states, carries a reduced static charge and has a soft, natural feel. While the amphoteric or anionic detergent surfactants of a shampoo permit satisfactory hair cleaning, it is however generally difficult to impart a pleasing permanently shaped form to the hair style after washing, without using additional compositions. In order to guarantee a satisfactory stylability of the hair and to make the hair style as permanent as possible after washing the hair, usually a hair fixing composition is applied after the hair washing with a shampoo in the form of an aqueous-alcoholic polymer solution, a gel, a foam or a hair spray, which are not washed out. This method is comparatively costly and time consuming for the user, since two compositions, a hair cleansing or cleaning composition and a hair fixing composition, are required and they must be used in two processes.

Hair cleansing compositions are known, which contain water-soluble cationic, anionic, amphoteric or nonionic polymers. Only a comparatively very weak fixing effect however is attained with these compositions, since the charges on the polymers facilitate a rinsing out of the fixing substances from the hair. The water-soluble polymers in these compositions primarily have a care effect.

Efforts were made to increase the fixing effect by adding fixing ingredients which were not soluble in the hair treatment composition. The disadvantage of these fixing agents was that they loaded the hair with a residue which results from multiple applications.

Another approach uses acrylate/silcone copolymers. Hydrophilic vinyl polymer backbone chains carrying hydrophobic side chains are known. The fixing obtained with this type of polymers is generally also comparatively weak, because they contain either anionic ethylenic unsaturated monomers (e.g. acrylic acid) or hydrophilic ethylenic unsaturated monomers (e.g. dimethylaminoethyl methacrylate) as disclosed in European Patent Documents EP-OS 412 704, EP-OS 412 707. This allows these polymers of course to be incorporated into shampoo formulations, but increases at the same time their solubility in water and thus their rinsiblity. The use of acrylate/silicone copolymers, which have hydrophilic vinyl polymer backbone chains and silicone side chains, for providing care properties in shampoos is described in WO 93/23009 and WO 95/03776. Fixing properties of these polymers in shampoo formulations were neither disclosed in WO 93/23009 nor in WO 95/03776.

WO 93/23009 and WO 95/03776 describe, among other things, the making of polymers, which have, in contrast to all the other above-described polymer types, a silicone backbone chain with acrylate side chains. Films of these polymers provide care properties because of their silicone backbone chain. The use of these nonionic hydrophobic polymers to obtain a hair care effect in largely water-free cosmetic formulations, such as lip stick, eye shadow pencil, antiperspirant sprays or in W/O emulsions, in which the hydrophobic polymer is dissolved in an oil phase, is described. Use of these polymers in shampoo formulations or a fixing action in combination with surfactant compounds was not described.

SUMMARY OF THE INVENTION

It is an object of the present invention to provide a hair cleansing composition which has an impressive hair fixing effect at the same time as a hair cleaning action, and which does not load the hair with an excessive build-up of residues even with multiple applications.

According to the invention this object is attain with a hair cleansing composition containing (a) at least one nonionic, water-insoluble vinyl/silicone copolymer having a backbone chain of siloxane polymer units and a side chain of vinyl polymer units, and (b) at least one detergent surfactant selected from the group consisting of nonionic, anionic, cationic and amphoteric surfactant compounds.

The vinyl/silicone copolymer is present in the composition according to the invention preferably in an amount of from 0.1 to 30 percent by weight and the surfactant preferably in an amount of from 3 to 50 percent by weight.

For example, suitable vinyl/silicone copolymer have the following general formula (I):

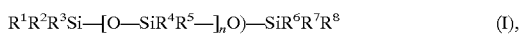

$$R^1R^2R^3Si\text{—}[O\text{—}SiR^4R^5\text{—}]_nO)\text{—}SiR^6R^7R^8 \qquad (I),$$

wherein the $R^1$ to $R^8$ groups are the same or different and, independently from each other, are selected from the group consisting of hydrogen, hydroxy, alkyl groups, aryl groups, alkylaryl groups, alkoxy groups, alkylamino groups, fluoroalkyl groups, and ZSA groups, in which Z represents a divalent connecting group selected from the group consisting of $C_1$- to $C_{10}$-alkylene groups, -alkarylene groups, -arylene groups and -alkoxyalkylene groups, preferably a methylene or propylene group; S represents sulfur; A is a vinyl polymer segment built up from nonionic monomer groups and n is a number greater than or equal to 5; with the proviso that at least one R group is a ZSA group.

Suitable nonionic vinyl polymer segment monomers A are preferably esters of methacrylic and acrylic acid with alcohols containing 1 to 18 carbon atoms, especially from 1 to 12 carbon atoms. These esters are generally weakly polar and the short to moderate chain length alcohol makes the polymer substantially water-insoluble. Suitable alcohols are, e.g., ethanol, 1-propanol, 2-propanol, 1-butanol, 1,1-dimethylethanol, 2-methyl-1-propanol, 1-pentanol, 2-pentanol, 3-pentanol, 2-methyl-1-butanol, 3-methyl-1-butanol, 2-hexanol, 3-methyl-1-pentanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol and the like.

Small amounts of copolymerizable monomers, such as styrene, vinyl ester, vinyl chloride, vinylidene chloride, acrylonitrile, methacrylonitrile, acryloxypropyltrimethoxysilane, methacryloxypropyltrimethoxysilane, other aryloyl monomers and similarly structured monomers, can be used.

For example, particularly preferred monomers which can be added include isooctylmethacrylate, isononylmethacrylate, 2-ethylhexylmethacrylate, laurylmethacrylate, i-pentyl-methacrylate, n-butylmethacrylate, i-butylmethacrylate, methylmethacrylate, ethylmethacrylate, t-butylmethacrylate, tridecylmethacrylate, stearylmethacrylate and similarly structured monomers and their mixtures.

Strongly polar, nonionic monomers can be copolymerized in small portions in the vinyl polymer segment A when the polymer according to the invention defined above remains substantially water-insoluble. For example, nonionic acrylate or methacrylate containing strongly polar, non-ionic monomers with at least one strongly polarizable group such as hydroxyl, alkoxyl, an amino group (primary, secondary or tertiary) or a alkenyl heterocyclic vinyl pyrrolidone or monomers with polyethylene oxide or polypropylene oxide side chains. The vinyl/silicone copolymer is however advantageously free of groups, which are present due to copolymerization of strongly polar, nonionic monomers in vinyl polymer segments A.

The vinyl polymer segment A of the vinyl/silicone copolymer is preferably free of anionic, cationic or amphoteric groups, which would reside therein by copolymerization of anionic, cationic or amphoteric monomers.

The vinyl/silicone copolymer according to the invention is made by a method described in WO 93/23009 and WO 95/03776.

Dimethylsiloxane/methyl-3-meracaptopropylsiloxane/isobutyl methacrylate copolymers (CFTA designation: Polysilicone-6) are particularly preferred as polymers for the hair treatment composition according to the invention.

A suitable product is, for example, sold under the tradename, Silicone "Plus" Polymer® VS 70 of 3M Corp., St. Paul, Minn., U.S.A.

The anionic surfactant compound of ingredient (b) is preferably selected from the group consisting of alkali or alkaline earth salts of the $C_{10}$- to $C_{18}$-alkyl sulfates, $C_{10}$- to $C_{18}$-alkylsulfonates, $C_{10}$- to $C_{18}$-alkylbenzene sulfonates, $C_{10}$- to $C_{18}$-xylene sulfonates, $C_{10}$- to $C_{18}$-alkylethersulfates ethoxylated with from 1 to 10 ethylene oxide units and the sulfosuccinic acid hemiesters of the general formula (II):

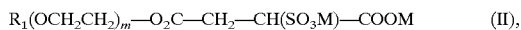

$$R_1(OCH_2CH_2)_m\text{—}O_2C\text{—}CH_2\text{—}CH(SO_3M)\text{—}COOM \qquad (II),$$

wherein $R_1$ means a $C_{10}$- to $C_{18}$-alkyl group, M was an alkali or alkaline earth cation and m is a whole number from 1 to 10, and the alkyl ether carboxylates of the general formula (III):

$$R_2(OCH_2CH_2)_n\text{—}OCH_2\text{—}COOM \qquad (III),$$

wherein $R_2$ represents a $C_{10}$- to $C_{18}$-alkyl group, M represents an alkaline or alkaline earth cation and n, a whole number from 1 to 20. The alkali and alkaline earth salts of the $C_{10}$- to $C_{18}$-alkylether sulfates ethoxylated with 1 to 10 ethylene oxide units are particularly preferred as the anionic surfactant ingredient.

The alkyl sulfates suitable as ingredient (b) of the composition according to the invention include sodium lauryl sulfate, which, for example, is marketed by Henkel KGaA, Düsseldorf, Germany under the trade name, Texapon® K12. The mixture of sodium salt of secondary $C_{12}$- to C16-alkane sulfates, which is marked by Hoechst AG, Frankfurt, Germany, under the trade name, Hostapur® SAS 30, in the form of a 30 percent solution, is one of the suitable alkyl sulfonate ingredients. The sodium salt of a linear dodecylbenzene sulfonate, which, e.g., is marketed in the form of a 55-percent paste under the trade name, Maranil® Paste A 55 of Henkel KGaA, Düsseldorf, Germany, is preferred as the alkylbenzene sulfonate ingredient. The sodium salt of xylene sulfonate, which is marketed, e.g., by the firm of Albright & Wilson Ltd., Cumbria, Great Britain, in the form of a solid under the trade name, Eltesol® SX 93, is preferred as the xylene sulfonate of the invention. The alkyl ether sulfates which are particularly preferred have a $C_{12}$-alkyl group and are ethoxylated with 3 ethylene oxide units. Lauryl ether sulfate ethoxylated with 3 ethylene oxide units, in the form of a 70% aqueous solution, marketed by Henkel KGaA, Düsseldorf, Germany, is for example suitable as ingredient (b) of the composition according to the invention. The preferred sulfosuccinic acid hemiesters are ethoxylated with three ethylene oxide units and have an alkyl group with twelve carbon atoms.

For example, a lauryl sulfosuccinic acid hemiester ethoxylated with 3 ethylene oxide units is sold by Henkel KGaA, Düsseldorf, Germany, in the form of a 40 percent aqueous solution of its disodium salt under the trade name, Texapon® SB3. The preferred alkyl ether carboxylates of ingredient (b) contained in the composition of the invention are ethoxylated with 10 ethylene oxide units and have an alkyl group with twelve carbon atoms. A lauryl carboxylate ethoxylated with 10 ethylene oxide units is marketed, for example, by the firm of Hüls AG Marl, Germany, under the trade name, Marlinat CM105/80, in the form of a 22 percent aqueous solution.

The nonionic surfactant compound of ingredient (b) is preferably selected from the group consisting of the ethoxylated fatty alcohols having from 12 to 18 carbom atoms, e.g. lauryl-, tetradecyl-, cetyl-, oleyl- and stearyl alcohol, alone or in mixture, ethoxylated with up to 40 Mol ethylene oxide per fatty alcohol; polyglyceryl ethers of saturated or unsaturated fatty alcohols and alkylphenols having 8 to 30 carbon atoms per alkyl group and 1 to 10 glyceryl units per molecule; fatty acid alkanol amides and ethoxylated sorbitan fatty acid ester. Also natural surfactant compounds, such as alkylpolyglucosides, which, for example, are marketed by the firm of Henkel, Germany, under the trade name, Planaren® APG 600 and natural surfactants, such as that marketed under the trademark Oramix® NS 10 of the firm of Seppic, are particularly preferred as nonionic surfactant compounds.

The amphoteric surfactant compounds of ingredient (b) are generally derivatives of aliphatic quaternary ammonium-, phosphonium- and sulfonium compounds of the formula (IV):

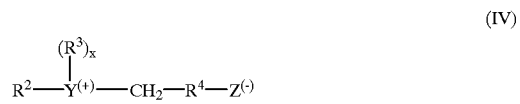

$$R^2\text{—}Y^{(+)}\overset{(R^3)_x}{\underset{|}{\text{—}}}CH_2\text{—}R^4\text{—}Z^{(-)} \qquad (IV)$$

wherein $R^2$ represents a straight chain or branched chain alkyl-, alkenyl- or hydroxyalkyl group with 8 to 18 carbon atoms and 0 to about 10 ethylene oxide units and 0 to 1 glyceryl units; Y is an N-, P- or S-containing group; $R^3$ represents an alkyl- or monohydroxyalkyl group with 1 to 3 carbon atoms; X=1 when Y is a sulfur atom and X=2 when Y is a nitrogen atom or a phosphorus atom; and $R^4$ is an alkyl or hydroxyalkyl group with 1 to 4 carbon atoms and Z is a carboxylate, sulfate, phosphonate or phosphate group.

Other suitable amphoteric surfactant compounds like betaine are also suitable in the hair cleansing composition according to the invention. For example, these betaines include $C_8$- to $C_{18}$-alkylbetaines, such as cocodimethylcarboxymethylbetaine, lauryldimethylcarboxymethylbetaine, lauryldimethylalphacarboxyethylbetaine, cetyldimethylcarboxymethylbetaine, oleyldimethylgammacarboxypropylbetaine and lauryl-bis-(2-hydroxypropyl)

alphacarboxyethylbetaine; $C_8$- to $C_{18}$-sulfobetaines, such as cocodimethylsulfopropylbetaine, stearyldimethylsulfopropylbetaine, lauryldimethylsulfoethylbetaine, lauryl-bis-(2-hydroxyethyl)sulfopropylbetaine; carboxyl derivatives of imidazole; $C_8$- to $C_{18}$-alkyldimethylammonium acetates, $C_8$- to $C_{18}$-alkyldimethylcarbonylmethylammonium salts and $C_8$- to $C_{18}$-fatty acid alkylamidobetaines, such as coconut oil fatty acid amidopropylbetaine, which for example is sold in the form of a 30 percent aqueous solution under the trade name, Tego Betaine® L7 of Th. Goldschmidt AG, Germany and N-coconut oil fatty acid amidoethyl-N-[2-(carboxymethoxy)-ethyl]glycerol (CFTA Name: cocoamphocarboxyglycinate), which for example is sold in the form of a 50 percent aqueous solution under the trade name, Miranol® C2M of Miranol Chemical Co. Inc., New Jersey, U.S.A.

Suitable cationic surfactants of ingredient (b) containing amino groups or quaternarized hydrophilic amino groups, which carry a positive charge in solution, have the following general formula (V),

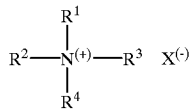

(V)

wherein $R^1$ to $R^4$ independently of each other are each selected from the group consisting of aliphatic groups with 1 to 22 carbon atoms, aromatic groups, alkoxy groups, polyoxyalkylene groups, alkylamido groups, hydroxyalkyl groups, aryl groups and alkarylgroups with from 12 to 22 carbon atoms and X represents an anion, for example, a halogen, acetate, phosphate, nitrate or alkyl sulfate anion. The aliphatic groups, in addition to carbon and hydrogen, can contain also bridging groups or other groups for example additional amino groups.

Examples of the cationic surfactants suitable as ingredient (b) include the chloride or bromide of alkydimethylbenzyl ammonium salts, alkyltrimethyl ammonium salts, e.g. cetyltrimethyl ammonium chloride or bromide, tetradecyltrimethyl ammonium chloride or bromide, alkyldimethylhydroxyethyl ammonium chloride or bromide, dialkyldimethyl ammonium chloride or bromide, alkylpyridinium salts, for example lauryl or cetylpyridinium chloride, alkylamidoethyltrimethyl ammonium ether sulfate and compounds with cationic character, such as amine oxides, e.g., alkylmethylamine oxide or alkyaminoethyldimethyl amine oxide. Cetyltrimethyl ammonium chloride, which for example is marketed in the form of a 26 percent aqueous solution under the trade name, Dehyquart® A of Henkel KGaA, Düsseldorf, Germany, and under the trade name, Genamin® CTAC of Hoechst AG, Frankfurt, Germany and in the form of a 50 percent solution in isopropanol under the trade name, Arquad® 16-50 of Akzo Chemicals GmbH, Düren, Germany, is especially preferred.

A preferred embodiment of the hair cleansing composition according to the invention contains in addition to ingredients (a) and (b) a solvent or a mixture of solvents with a boiling point under 400° C. in an amount of from 0.5 to 90 percent by weight, advantageously from 10 to 50 percent. Branched or unbranched hydrocarbons with 5 to 15 carbon atoms, such as pentane, hexane, isopentane and cyclic hydrocarbons, such as cyclopentane and cyclohexane are suitable, whereas pentane is particularly preferred. Straight chain, cyclic or branched chain alcohols, such as ethanol and isopropanol are particularly preferred. High boiling solvents, such as ethylene glycol or propylene glycol, are also suitable. Especially the hair treatment composition according to the invention can be used in aerosol form. Propellant gases, such as propane-butane, dimethyl ether or fluorinated hydrocarbons, can be used as propellant means with partial solvent character. The propellant gases can be employed in an amount of from about 3 to 90 percent by weight, preferably from 5 to 15 percent by weight.

A further preferred embodiment of the hair cleansing composition according to the invention contains, in addition, at least one additional silicone derivative. Suitable silicone derivatives are, e.g., linear polydimethylsiloxane (CTFA-designation: dimethicone), cyclic polydimethyl siloxane (CTFA-designation: cyclomethicone); polydimethylsiloxane with hydroxy end groups (CTFA-designation: dimethiconole) or dimethylsiloxaneglycol copolymers (CFTA-designation dimethicone copolyol). Polydimethylsiloxanes are, for example, sold under the trade names, Dow Corning Silicone Fluids 200, 225, 244, 245, 344, 345, VS-7207, VS-7349, VS-7158 of Dow Corning, U.S.A.; Abil® K4, Abil® 10-10000 of Goldschmidt, Germany; GE Silicone SF 1202 or 1173 of GE Silicone, U.S.A. or Belsil® DMC of Wacker, Germany. Dimethylsilioxaneglycol copolymers are, for example, marketed under the trade names, Abil® Polyetherpolysiloxane of Goldschmidt, Germany; Silwet-L of Union Carbide, U.S.A. or silicone fluids 190, 193, Q2-5520 of Dow Corning, U.S.A. Cetyl dimethicone or cetyl dimethicone copolyol can also be contained in the composition of the invention.

The polydimethylsiloxanes with hydroxyl end groups (Dimethiconoles) are particularly preferred silicone derivatives. Suitable dimethiconoles are, for example, sold under the trade name, silicone fluid F 212 or Silicone oil CT 601 M of Wacker, Germany; Silicone Fluid Series NM 201-50000 of Hüls, Germany, S-series of Siltech, U.S.A. and Unisil SF-R of UPI, U.S.A. Suitable mixtures with volatile cyclomethicones or dimethicones include the commercial products Dow Corning Q2-1401 and Dow Corning Q2-1403 of Dow Corning, U.S.A. and Abil® OSW 12 and 13 of Goldschmidt, Germany. The fixing properties of the hair cleansing composition according to the invention are augmented by the dimethiconole content and the residue behavior is positively effected.

Polymers with a strong thickening effect can be contained in the hair cleansing composition in amounts of from 0.01 to 20 percent by weight in addition to the ingredients (a) and (b). For example, homopolymers of acrylic acid with a molecular weight of from 2,000,000 to 6,000,000, which, e.g., are sold by BF Goodrich, Cleveland, U.S.A. under the trade name, Carbopol®, are suitable polymers with a strong thickening effect. Polymers of acrylic acid and acrylamide (sodium salt), sold under the trade name, Hostacerin® PN 73 by Hoechst, Germany, with a molecular weight of 2,000,000 to 6,000,000, guar gum, 2-hyddroxypropyl ether substituted guar gum (CFTA-designation: hydroxypropyl guar), karaya gum, xanthan gum and sclerotium gum, sold by the firm of Alban Muller, Montreuil, France, under the trade name Amigel® are other examples. Additional thickeners include the copolymers of acrylic acid or methacrylic acid, such as those sold under the trade name Carbopol 1342 or Pemulen TR1 of Goodrich, U.S.A. The composition according to the invention preferably contains 2-hydroxy-3-(trimethylammonium chloride)propyl ether substituted guar gum (CTFA-dsignation: guar hydroxypropyltrimonium chloride) or thickened cellulose ether, such as hydroxypropyl cellulose, hydroxyethyl cellulose, in an amount of from about 0.05 to 5 percent by weight, such as that sold under the trade name, Natrosol 250 HHR of the firm of Aqualon.

In addition to the ingredients (a) and (b) the hair cleansing composition according to the invention can contain anionic, cationic, amphoteric or nonionic film-forming polymers, in an amount of from 0.01 to 20 percent by weight, which dissolve in the formulation, partially precipitate or remain undissolved and have film-forming or thickening or viscosity lowering effects. The anionic or cationic and amphoteric polymers can be present unneutralized, partially neutralized or completely neutralized. All synthetic, natural or chemically modified natural polymers can be used, which are compatible with the ingredients of the hair treatment composition according to the invention.

Suitable nonionic polymers include, for example, polyvinylpyrrolidone polymers, which are sold under the trade name, Luviskol®, by BASF AG, Ludwigshafen, Germany; copolymerizates of vinylpyrrolidone and vinyl acetate, which, e.g., are sold under the trade name, Luviskol® VA, by BASF AG, Ludwigshafen, Germany; terpolymers of vinyl pyrrolidone, vinyl acetate and vinyl propionate, which, e.g., are sold under the tradename, Luviskol® VAP, by BASF AG, Ludwigshafen, Germany; polyacrylamide, which for example is sold under the trade name, Akypomine® P191 of CHEM-Y, Emmerich, Germany or Sepigel® 305 of Seppic, U.S.A; polyvinyl alcohols, which for example is marketed under the trade name, Elvanol® of DuPont or Vinol® 523/540 of Air Products, U.S.A. and polyethylene glycol with a molecular weight of from 800 to 20,000 g/mol, which is marketed for example under the trade name, Lipoxol® 1000 of Hüls AG, Germany; Pluracol E 4000 of BASF, Germany or Upiwax® 20,000 of UPI. The homopolymers of N-vinylformamide, such as those sold under the trade name PVF of National Starch, U.S.A. are also suitable. The nonionic polymers having natural origins include, for example, hydroxypropyl chitosan.

Suitable anionic polymers include crotonic acid-vinyl acetate copolymers, which for example are sold in the form of a 60 percent solution in isopropanol/water under the trade name, Aristoflex® of Hoechst, Germany. Additional suitable anionic polymers include, for example, terpolymers of acrylic acid, ethyl acrylate and N-t-butylacrylamide, such as those sold under the trade name, Ultrahold 8 and Ultrahold Strong of BASF, Ludwigshafen, Germany.

Suitable cationic polymers include vinylpyrrolidone/methacrylamidopropyltrimethylammonium chloride copolymers, such as those sold under the trade name, Gafquat® of Gaf Co., New York, U.S.A. Additional cationic polymers are for example the copolymers of polyvinylpyrrolidone and imidazoliminmethochloride, marketed under the trade name, Luviquat® HM 550 by BASF AG, Ludwigshafen, Germany; the terpolymer of dimethyldiallylammonium chloride, sodium acrylate and acrylamide, marketed under the trade name Merquat® Plus 3300 of Calgon, Pittsburgh, U.S.A.; the terpolymer of vinylpyrrolidone, dimethylaminoethylmethacrylte and vinylcaprolactam, sold by ISP, U.S.A. under the trade name Gaffix® VS 713; the quaternary ammonium salt of hydroxyethyl cellulose and a trimethylammonium-substituted epoxide, marketed under the trade name Polymer® JR of Amercol, Edison, U.S.A.; vinylpyrrolidone/methacrylamidopropyltrimethylammonium chloride copolymer marketed under the trade name, Gafquat® HS 100 by Gaf, and diquaternary polydimethylsiloxane marketed under the trade name, Abil® Quat 3272 of Goldschmidt, Germany.

Suitable amphoteric polymers include for example copolymers of octylacrylamide, t-butylaminoethylmethacrylate and one or more monomers selected from the group consisting of acrylic acid, methacrylic acid or their esters, such as those obtainable from National Starch, Great Britain, under the trade name, Amphomer® 28-4910 or Amphomer LV-71 of National Starch, Great Britain. For example, suitable natural polymers, which are present in the hair treatment cleansing according to the invention in amounts of from 0.1 to 15 percent by weight, can include low weight molecular and high molecular weight chitosan, which, e.g., is sold by Kyowa Oil & Fat, Japan. Different saccharides can also be used, such as polysaccharides or mixtures of oligo-, mono- and disaccharides, which are sold for example under the trade name C-PUR® of Cerestar, Brüssels, Belgium.

Understandably the hair cleansing composition according to the invention can contain the usual conventional additive ingredients used for hair cleansing compositions and styling compositions including: propellants, such as ethylene glycol distearate, in an amount of from about 0.5 to 5.0 percent by weight; pearlescence-inducing agents, such as a mixture of fatty acid monoalkylolamides/ethyleneglycoldistearates, in an amount of from about 1.0 to 10.0 percent by weight; preservative materials, such as 2,2,4-trichloro-2-hydroxydiphenyl ether, methylchloroisothiazolinone, p-hydroxybenzoic acid ester, sorbic acid, salicylic acid, mandelic acid or formic acid, in an amount of from about 0.01 to 1.0 percent by weight; thickeners, such as glycerol monolaurate, coconut oil fatty acid diethanol amides; sodium chloride, in an amount of from about 0.5 to 3.0 percent by weight; diluents or thinning agents, such as 1,2-propyleneglycol or ethoxylated sorbitan monolaurate, in an amount of from about 0.5 to 5.0 percent by weight; light protective agents; luster-imparting agents; buffer substances, such as sodium citrate or sodium phosphate, in an amount of from about 0.1 to 1.0 percent by weight; solvating agents, such as ethoxylated, if necessary hydrogenated, castor oil, in an amount of from about 0.1 to 1.0 percent by weight; and antioxidants, such as tocopherol, in an amount of from about 0.01 to 1 percent by weight and dye compounds, such as fluorescein sodium salt, in an amount of from about 0.1 to 1.0 percent by weight. Also the hair cleansing composition according to the invention can contain care and moisturizing compositions, such as 1,2-propandiol and glycerol or conditioning additives. For example compounds, which have an impressive substantivity in the hair, can be included in the compositions of the invention as conditioning additives. These compounds include the quaternary ammonium salts of guar, amidomethicone, dimethicone copolyol phosphate, dimethicone/disodium PG-propyldimethicone thiosulfate copolyol (for example Abil S 255 of Goldschmidty AG, Germany), dimethicone propyl PG betaine (for example Abil B 9950 of Goldschmidt AG, Germany), in an amount of about 0.01 to 10 percent by weight. Oils, waxes or fatty acids, e.g. jojoba oil or fruit wax, which are obtained from plant or animal raw materials, are suitable for example for care additives.

The water content of the hair cleansing composition according to the invention is, for example, advantageously between 15 to 80 percent by weight.

The composition according to the invention preferably has a pH of from 4 to 9, especially preferably from 4.5 to 7.5. The adjustment of the pH of the composition according to the invention can take place for example with citric acid, phosphoric acid, hydrochloric acid or sodium hydroxide.

The hair cleaned with the composition according to the invention has a good wet and dry combability, may be satisfactorily styled, and is definitely and detectably fixed. The hair is not loaded and the natural feel of the hair is not impaired.

The following examples should illustrated the subject matter of the invention.

EXAMPLES

Example 1: Hair cleansing composition with anionic surfactant

| | |
|---|---|
| 10.0 g | dimethylsiloxane/methyl-3-mercaptopropylsiloxane/ isobutylmethacrylate copolymer, 25% in cyclomethicone (Polymer Plus VS70 of 3M Corp., USA) |
| 8.4 g | lauryl ether sulfate |
| 1.0 g | hydroxyethylcellulose (Natrosol ® 250 HHR of Aqualon/Netherlands) |
| 20.0 g | isopropanol |
| 60.6 g | water |
| 100.0 g | |

Example 2: Hair cleansing composition with anionic and amphoteric surfactant

| | |
|---|---|
| 10.0 g | dimethylsiloxane/methyl-3-mercaptopropylsiloxane/ isobutylmethacrylate copolymer, 25% in cyclomethicone (Polymer Plus VS70 of 3M Corp., USA) |
| 7.0 g | lauryl ether sulfate |
| 1.5 g | coconut oil fatty acid amidopropylbetaine |
| 1.0 g | 2-hydroxy-3-(trimethylammonium chloride)propyl ether substituted guar gum |
| 20.0 g | isopropanol |
| 60.5 g | water |
| 100.0 g | |

Example 3: Hair cleansing composition with amphoteric surfactant

| | |
|---|---|
| 10.0 g | dimethylsiloxane/methyl-3-mercaptopropylsiloxane/ isobutylmethacrylate copolymer, 25% in cyclomethicone (Polymer Plus VS70 of 3M Corp., USA) |
| 9.0 g | coconut oil fatty acid amidopropylbetaine |
| 1.0 g | 2-hydroxy-3-(trimethylammonium chloride)propyl ether substituted guar gum |
| 20.0 g | isopropanol |
| 60.0 g | water |
| 100.0 g | |

Example 4: Hair cleansing composition with anionic and nonionic surfactant

| | |
|---|---|
| 10.0 g | dimethylsiloxane/methyl-3-mercaptopropylsiloxane/ isobutylmethacrylate copolymer, 25% in cyclomethicone (Polymer Plus VS70 of 3M Corp., USA) |
| 7.0 g | lauryl ether sulfate |
| 2.75 g | decyl glucoside |
| 1.0 g | hydroxyethylcellulose (Natrosol ® 250 HHR of Aqualon/Netherlands) |
| 0.5 g | polydimethylsiloxane (Silicone Fluids 225, Dow Corning, USA) |
| 0.5 g | dimethicone copolyol (Silwet-copolymer L 7604 of Union Carbide, USA) |
| 20.0 g | isopropanol |
| 58.25 g | water |
| 100.0 g | |

Example 5: Hair cleansing composition with amphoteric and nonionic surfactant

| | |
|---|---|
| 10.0 g | dimethylsiloxane/methyl-3-mercaptopropylsiloxane/ isobutylmethacrylate copolymer, 25% in cyclomethicone (Polymer Plus VS70 3M Corp., USA) |
| 10.0 g | lauryl glucoside |
| 6.0 g | coconut oil fatty acid amidopropylbetaine |
| 1.0 g | 2-hydroxy-3-(trimethylammoniumchloride)propyl ether substituted guar gum |
| 20.0 g | isopropanol |
| 52.0 g | water |
| 100.0 g | |

Example 6: Hair cleansing composition with anionic surfactant in aerosol form

| | |
|---|---|
| 10.0 g | dimethylsiloxane/methyl-3-mercaptopropylsiloxane/ isobutylmethacrylate copolymer, 25% in cyclomethicone (Polymer Plus VS70 3M Corp., USA) |
| 8.4 g | lauryl ether sulfate |
| 1.0 g | hydroxyethylcellulose (Natrosol ® 250 HHR Aqualon, Netherlands) |
| 0.5 g | dimethiconol, 13% in cyclomethicone (Abil ® OSW 13 of Goldschmidt, Germany) |
| 30.0 g | isopropanol |
| 10.0 g | propane-butane propellant gas mixture |
| 40.1 g | water |
| 100.0 g | |

Example 7: Hair cleansing composition with anionic surfactant and amphoteric surfactant in aerosol form

| | |
|---|---|
| 10.0 g | dimethylsiloxane/methyl-3-mercaptopropylsiloxane/ isobutylmethacrylate copolymer, 25% in cyclomethicone (Polymer Plus VS70 3M Corp., USA) |
| 5.6 g | lauryl ether sulfate |
| 3.0 g | coconut oil fatty acid amidopropylbetaine |
| 1.0 g | 2-hydroxy-3-(trimethylammoniumchloride)propyl ether substituted guar gum |
| 30.0 g | isopropanol |
| 10.0 g | propane-butane propellant gas mixture |
| 40.2 g | water |
| 100.0 g | |

Example 8: Hair cleansing composition with anionic and nonionic surfactant in aerosol form

| | |
|---|---|
| 10.0 g | dimethylsiloxane/methyl-3-mercaptopropylsiloxane/ isobutylmethacrylate copolymer, 25% in cyclomethicone (Polymer Plus VS70 of 3M Corp., USA) |
| 5.6 g | lauryl ether sulfate |
| 5.5 g | decyl glucoside |
| 1.0 g | hydroxyethylcellulose (Natrosol ® 250 HHR of Aqualon, Netherlands) |

-continued

| | |
|---|---|
| 30.0 g | isopropanol |
| 10.5 g | propane-butane propellant gas mixture |
| 27.4 g | water |
| 100.0 g | |

Example 9: Hair cleansing composition with pentane additive

| | |
|---|---|
| 10.0 g | dimethylsiloxane/methyl-3-mercaptopropylsiloxane/isobutylmethacrylate copolymer, 25% in cyclomethicone (Polymer Plus VS70 of 3M Corp., USA) |
| 8.4 g | lauryl ether sulfate |
| 1.0 g | hydroxyethylcellulose (Natrosol ® 250 HHR of Aqualon, Netherlands) |
| 1.0 g | laurylmethicone copolyol (Dow Corning Q2-5200 of Dow Corning, Europe, Belgium) |
| 20.0 g | isopropanol |
| 20.0 g | pentane |
| 39.6 g | water |
| 100.0 g | |

Example 10: Hair cleansing composition with pentane additive in aerosol form

| | |
|---|---|
| 10.0 g | dimethylsiloxane/methyl-3-mercaptopropylsiloxane/isobutylmethacrylate copolymer, 25% cyclomethicone (Polymer Plus VS70 of 3M Corp., USA) |
| 8.4 g | lauryl ether sulfate |
| 1.0 g | hydroxyethylcellulose (Natrosol ® 250 HHR of Aqualon/Netherlands) |
| 0.5 g | dimethiconol, 13% in cyclomethicone (Dow Corning 1401, Dow Corning, Europe, Belgium) |
| 0.5 g | laurylmethicone copolyol (Dow Corning Q2-5200, Dow Corning, Europe, Belgium) |
| 20.0 g | isopropanol |
| 20.0 g | pentane |
| 39.6 g | water |
| 100.0 g | |

Example 11: Hair cleansing composition in 2-component form

Component 1:

| | |
|---|---|
| 10.0 g | dimethylsiloxane/methyl-3-mercaptopropylsiloxane/isobutylmethacrylate copolymer, 25% in cyclomethicone (Polymer Plus VS70 of 3M Corp., USA) |
| 2.0 g | acrylate/$C_{10}$–$C_{30}$-alkylacrylate crosspolymer (Pemulen TR-1 of Goodrich, USA) |
| 1.0 g | dimethiconol, 13% in cyclomethicone (Dow Corning 1401 of Dow Corning, Europe, Belgium) |
| 40.0 g | isopropanol |
| 47.0 g | water |
| 100.0 g | |

Component 2: lauryl ether sulfate, 28% in water

When component 1 is applied together with component 2 to the hair, an effect occurs according to the above-described advantages of the hair treatment composition of the present invention.

Example 12: Hair cleansing composition with anionic surfactant

| | |
|---|---|
| 10.0 g | dimethylsiloxane/methyl-3-mercaptopropylsiloxane/isobutylmethacrylate copolymer, 25% in cyclomethicone (Polymer Plus VS70 of 3M Corp., USA) |
| 8.4 g | lauryl ether sulfate |
| 1.0 g | dimethiconol, 13% in cyclomethicone (Dow Corning 1401 of Dow Corning, Europe, Belgium) |
| 1.0 g | hydroxyethylcellulose (Natrosol ® 250 HHR Aqualon/Netherlands) |
| 20.0 g | isopropanol |
| 59.6 g | water |
| 100.0 g | |

Example 13: Hair cleansing composition with anionic and amphoteric surfactant

| | |
|---|---|
| 10.0 g | dimethylsiloxane/methyl-3-mercaptopropylsiloxane/isobutylmethacrylate copolymer, 25% in cyclomethicone (Polymer Plus VS70 of 3M Corp., USA) |
| 7.0 g | lauryl ether sulfate |
| 1.5 g | coconut oil fatty acid amidopropylbetaine |
| 1.0 g | dimethiconol, 13% in cyclomethicone (Dow Corning 1401 of Dow Corning, Europe, Belgium) |
| 1.0 g | 2-hydroxy-3-(trimethylammonium chloride)propyl ether substituted guar gum |
| 20.0 g | isopropanol |
| 59.5 g | water |
| 100.0 g | |

Example 14: Hair cleansing composition with amphoteric surfactant

| | |
|---|---|
| 10.0 g | dimethylsiloxane/methyl-3-mercaptopropylsiloxane/isobutylmethacrylate copolymer, 25% in cyclomethicone (Polymer Plus VS70 of 3M Corp., USA) |
| 9.0 g | coconut oil fatty acid amidopropylbetaine |
| 1.0 g | dimethylsiloxaneglycol copolymer (Silwet ® copolymer PC 90, of Union Carbide, USA) |
| 1.0 g | 2-hydroxy-3-(trimethylammonium chloride)propyl ether substituted guar gum |
| 20.0 g | isopropanol |
| 59.0 g | water |
| 100.0 g | |

Example 15: Hair cleansing composition with amphoteric and nonionic surfactant

| | |
|---|---|
| 10.0 g | dimethylsiloxane/methyl-3-mercaptopropylsiloxane/isobutylmethacrylate copolymer, 25% in cyclomethicone (Polymer Plus VS70 of 3M Corp., USA) |
| 10.0 g | lauryl glucoside |
| 6.0 g | coconut oil fatty acid amidopropylbetaine |
| 1.0 g | dimethiconol, 13% in cyclomethicone (Dow Corning 1401 of Dow Corning, Europe, Belgium) |
| 1.0 g | 2-hydroxy-3-(trimethylammonium chloride)propyl ether substituted guar gum |
| 20.0 g | isopropanol |
| 51.0 g | water |
| 100.0 g | |

Example 16: Hair cleansing composition with anionic surfactant and amphoteric surfactant in aerosol form

| | |
|---|---|
| 10.0 g | dimethylsiloxane/methyl-3-mercaptopropylsiloxane/ isobutylmethacrylate copolymer, 25% in cyclomethicone (Polymer Plus VS70 of 3M Corp., USA) |
| 5.6 g | lauryl ether sulfate |
| 3.0 g | coconut oil fatty acid amidopropylbetaine |
| 1.0 g | 2-hydroxy-3-(trimethylammonium chloride)propyl ether substituted guar gum |
| 0.5 g | dimethiconol, 13% in cyclomethicone (Abil ® OSW13 of Goldschmidt/Germany) |
| 30.0 g | isopropanol |
| 10.0 g | propane-butane propellant gas mixture |
| 39.7 g | water |
| 100.0 g | |

Example 17: Hair cleansing composition with anionic and nonionic surfactant in aerosol form

| | |
|---|---|
| 10.0 g | dimethylsiloxane/methyl-3-mercaptopropylsiloxane/ isobutylmethacrylate copolymer, 25% in cyclomethicone (Polymer Plus VS70 of 3M Corp., USA) |
| 5.6 g | lauryl ether sulfate |
| 5.5 g | decyl glucoside |
| 1.0 g | hydroxyethylcellulose (Natrosol ® 250 HHR Aqualon/Netherlands) |
| 0.5 g | dimethylpolysiloxane (viscosity 500 mPa · s at 25° C.) |
| 30.0 g | isopropanol |
| 10.5 g | propane-butane propellant gas mixture |
| 26.9 g | water |
| 100.0 g | |

Unless otherwise indicated all percents are percents by weight.

The disclosure in German Patent Application 196 42 623.5 of Oct. 16, 1996 is incorporated here by reference. This German Patent Application describes the invention described hereinabove and claimed in the claims appended hereininbelow and provides the basis for a claim of priority for the instant invention under 35 U.S.C. 119.

While the invention has been illustrated and described as embodied in a hair cleansing composition with fixing properties, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention. What is claimed is new and is set forth in the following appended claims.

We claim:

1. A hair cleansing composition containing from 0.1 to 30 percent by weight of at least one vinyl/silicone copolymer consisting of a dimethylsiloxane/methyl-3-mercaptopropylsiloxane/isobutyl-methacrylate copolymer and from 3 to 50 percent by weight of at least one detergent surfactant selected from the group consisting of nonionic, anionic, cationic and amphoteric surfactant compounds.

2. The hair cleansing composition as defined in claim 1, further comprising at least one silicone compound.

3. The hair cleansing composition as defined in claim 2, wherein said at least one silicone compound is selected from the group consisting of polydimethylsiloxanes without hydroxy terminal groups, polydimethylsiloxanes with hydroxy terminal groups and dimethylsiloxane glycol copolymers.

4. The hair cleansing composition as defined in claim 2, wherein said at least one silicone compound consists of at least one polydimethylsiloxane with hydroxy terminal groups.

5. The hair cleansing composition as defined in claim 2, containing from 0.1 to 40 percent by weight of said at least one silicone compound.

6. The hair cleansing composition as defined in claim 1, further comprising at least one straight or branched chain hydrocarbon having from 5 to 15 carbon atoms.

* * * * *